US012721622B2

(12) United States Patent
Suzuki et al.

(10) Patent No.: US 12,721,622 B2
(45) Date of Patent: Sep. 1, 2026

(54) MEDICAL SUTURE NEEDLE

(71) Applicant: MANI, INC., Utsunomiya (JP)

(72) Inventors: Yasushi Suzuki, Utsunomiya (JP); Mitsuhiro Kakinuma, Utsunomiya (JP); Masato Mizui, Utsunomiya (JP)

(73) Assignee: MANI, INC., Utsunomiya (JP)

( * ) Notice: Subject to any disclaimer, the term of this patent is extended or adjusted under 35 U.S.C. 154(b) by 586 days.

(21) Appl. No.: 17/623,581

(22) PCT Filed: Aug. 24, 2020

(86) PCT No.: PCT/JP2020/031903
§ 371 (c)(1),
(2) Date: Dec. 28, 2021

(87) PCT Pub. No.: WO2021/039743
PCT Pub. Date: Mar. 4, 2021

(65) Prior Publication Data
US 2022/0249089 A1 Aug. 11, 2022

(30) Foreign Application Priority Data
Aug. 28, 2019 (JP) ................................ 2019-155257

(51) Int. Cl.
*A61B 17/06* (2006.01)

(52) U.S. Cl.
CPC .................. *A61B 17/06066* (2013.01); *A61B 2017/06071* (2013.01)

(58) Field of Classification Search
CPC .......... A61B 17/06066; A61B 17/3417; A61B 2017/3454–346; D05B 85/00–14
See application file for complete search history.

(56) References Cited

U.S. PATENT DOCUMENTS 5,403,344 A 4/1995 Allen
5,797,961 A * 8/1998 Smith ............. A61B 17/06066 112/222

(Continued)

FOREIGN PATENT DOCUMENTS

EP 0582276 2/1994
JP H09-322898 A 12/1997

(Continued)

OTHER PUBLICATIONS

International Search Report mailed Oct. 13, 2020, issued in corresponding International Application No. PCT/JP2020/031903, filed Aug. 24, 2020, 2 pages.

(Continued)

*Primary Examiner* — Elizabeth Houston
*Assistant Examiner* — Jonathan A Hollm
(74) *Attorney, Agent, or Firm* — CHRISTENSEN O'CONNOR JOHNSON KINDNESS PLLC

(57) ABSTRACT

Provided is a medical suture needle configured so as to reduce the risk of bending and cracks occurring in a tip part in which a point is formed. The medical suture needle includes a cutting blade section (10) and a body section (20) that is continuous with the cutting blade section. The cutting blade section comprises one bottom surface (11) and two inclined surfaces (12) and includes a point (13) at which the one bottom surface and the two inclined surfaces meet, a cutting blade (14) formed so as to be continuous from the point and such that the bottom surface and the inclined surfaces meet, and a ridge (15) formed so as to be continuous from the point and such that the two inclined surfaces meet. The thickness of the cutting blade section decreases from the body section toward the point. The two inclined surfaces include grooves (18) that have a curved surface shape, that each have a preset size, and that are formed along the ridge (Continued)

starting from the position of the cutting blade so as to be separated from the point by a predetermined distance. The lower edges (18*c*) of the grooves separate from the cutting blade toward the ridge side as the grooves approach the body section side in the end sections of said grooves on the body section side.

3 Claims, 6 Drawing Sheets

(56) References Cited

U.S. PATENT DOCUMENTS

| | | | | |
|---|---|---|---|---|
| 2012/0259359 | A1* | 10/2012 | Uetake | B21G 1/08 606/223 |
| 2017/0252037 | A1 | 9/2017 | Matsutani et al. | |
| 2019/0008513 | A1 | 1/2019 | Ishida et al. | |

FOREIGN PATENT DOCUMENTS

| | | | |
|---|---|---|---|
| JP | 2001-333910 | A | 12/2001 |
| JP | 2001333909 | | 12/2001 |
| JP | 2010154961 | | 7/2010 |
| JP | 2010172533 | A | 8/2010 |
| JP | 4576589 | B2 | 11/2010 |
| JP | 2016049173 | A | 4/2016 |
| JP | 2017-121312 | A | 7/2017 |
| JP | 2009-165638 | A | 7/2019 |

OTHER PUBLICATIONS

Office Action issued May 25, 2022 in corresponding Indian Application No. 202147059017, filed Dec. 17, 2021, 5 pages.

Office Action for CN 202080046430.0, mailed Oct. 30, 2023 (14 pages).

* cited by examiner

MEDICAL SUTURE NEEDLE

TECHNICAL FIELD

The present invention relates to a medical suture needle for suturing living tissue, and in particular to a medical suture needle for reducing a risk of bending and cracking of a tip portion including a sharp pointed end.

BACKGROUND ART

A plurality of types of medical suture needles having optimum shapes corresponding to desired suture sites have been provided. Among them, there are medical suture needles having sharp pointed ends and cutting-edge portions having continuous cuttings edge from the pointed ends, in which the cutting-edge portion has a triangular cross-section.

For example, the medical suture needle described in Patent Document 1 has a first cutting-edge portion, a second cutting-edge portion, and a third cutting-edge portion in a cutting-edge section having a triangular cross-section. The first cutting-edge portion has cutting-edges at each side portion, and a top part having no cutting-edge. The second cutting-edge portion has: the first recesses formed by moving slopes on both side portions of a circumferential surface parallel to the center of the triangle; side cutting-edges formed by the first recesses; and a mountain-shaped cutting-edge provided at a top part formed by the first recesses. Further, in the third cutting-edge portion, side cutting-edges formed on both side portions of a circumferential surface and a mountain-shaped cutting-edge formed on a top part with each cutting-edge forming the second cutting-edge portion maintaining a respective angle.

Patent Document 1 discloses that even if edge angle between the mountain-shaped cutting-edge and each side cutting-edge of the second cutting-edge portion is made relatively small, high bending strength can be obtained by increasing a thickness, and that in the third cutting-edge portion, even if the edge angle between each side cutting-edge and the mountain-shaped cutting-edge is made relatively small by the second recess, it can be formed continuously to the needle tip in a sharp state and insertion property can be obtained.

A medical suture needle described in Patent Document 2 has a cutting-edge having a first angle and a second angle, in which a three cutting-edges are radially arranged by connecting them through a connecting surface. The medical suture needle can improve insertion property when suturing biological tissue.

Since the technologies described in the above Patent Documents 1 and 2 have three cutting-edges which are radially arranged, high insertion property can be obtained. However, thickness of the central portion of the cross-sectional area is thin, which may reduce strength.

The present applicant has developed a medical suture needle described in Patent Document 3 in order to solve the above problems. The medical suture needle has a cutting-edge section having a sharp pointed end, a first cutting-edge portion formed from the pointed end to a body portion, and a second cutting-edge portion. The first cutting-edge portion has two first slopes and one first bottom surface, and has a triangular cross-section formed by the slopes and bottom surface. The second cutting-edge portion has two first slopes, a second slope formed on each of the first slopes, and one first bottom surface. In particular, when the third cutting-edge portion is configured to be continuous with a body side of the second cutting-edge portion, the third cutting-edge portion has a groove having a slope smaller than an angle of the first slope on the two first slopes.

Thus, the first cutting-edge portion has a triangular cross-section formed by the two slopes and one bottom surface and a cutting-edge formed on the edge where the bottom surface intersects with the slope, so that a thickness of the central portion does not become thin, and strength of a tip portion can be improved. In particular, since the cutting-edge formed in the third cutting-edge portion has a smaller cutting-edge angle than that formed in the first cutting-edge portion, good insertion property can be secured.

PRIOR ARTS

Patent Documents

Patent Document 1 JP2009-165638A (U.S. Pat. No. 4,576,589)
Patent Document 2 U.S. Pat. No. 5,403,344
Patent Document 3 JP2017-121312A

DISCLOSURE OF THE INVENTION

Problem to be Solved by the Invention

However, even the medical suture needle described in Patent Document 3 is not entirely free of problems, which has several points to be improved. For example, since the cutting-edge in the second cutting-edge portion is formed at the edge where the second bottom surface intersects with the second slope, the angle of the edge is larger than that of the edge of the first cutting-edge portion, which may reduce the incisiveness of the biological tissue.

In the third cutting-edge portion, the groove having the angle smaller than that of the first slope is formed on the first slope, the third slope is formed on the lower edge of the groove, and the cutting-edge is formed on the edge where the third slope intersects with the third bottom surface. The angle of the edge of the third cutting-edge is smaller than that of the edge of the first cutting-edge portion. In addition, the second slopes in the second cutting-edge portion which have the angles smaller than that of the first slopes formed on both sides of a top part, the slopes that make up the grooves portion, and the third slope in the third cutting-edge, are formed by press working. For this reason, the processing rate of the third cutting-edge portion is particularly high, and cracks are more likely to occur on the third cutting-edge portion.

It is an object of the present invention to provide a medical suture needle for reducing a risk of bending and cracking of a tip portion including a sharp pointed end.

Means of Solving the Problems

In order to solve the above problems, an exemplary medical suture needle according to the present invention includes a cutting-edge portion and a body portion continuously connected to the cutting-edge portion, in which the cutting-edge portion includes:

one bottom part;

two slopes;

a sharp pointed end configured by convergence of the bottom part and the two slopes;

cutting-edges extending from the sharp pointed end, each cutting-edge being configured by connection of the bottom part and each slope; and a top part extending from the sharp pointed end and configured by connection of the two slopes, thickness of the cutting-edge portion decreases from the body portion to the sharp pointed end, each slope comprises a curved groove having a predetermined dimension, each curved groove extends, along the top part, from a position on the cutting-edge isolated from the sharp pointed end by a predetermined distance, and a lower portion of each curved groove is isolated from the cutting edge toward the top part as the lower portion extends from a position on a body-portion-side end of each curved groove toward the body portion.

Effects of the Invention

In the medical suture needle of the present invention (hereinafter simply referred to as the "suture needle"), each slope constituting the cutting-edge portion has the curved groove, in which the curved groove extends, along the top part, from a position on the cutting-edge isolated from the sharp pointed end by a predetermined distance. As a result, each cutting-edge configured by intersection of the bottom part and each curved groove can have a sharp angle.

In particular, each curved groove has a curved surface configured along the top porting while maintaining predetermined dimensions, and the lower portion of the curved groove is isolated from each cutting-edge toward the top part, from a position on a body-portion-side end of each curved groove toward the body portion. Therefore, compared with the suture needle described in Patent Document 3, the processing rate for the cutting-edge portion can be reduced, and the risk of cracking of the cutting-edge portion can be reduced. Therefore, the risk of cracking or bending can be reduced when a force is applied to the tip portion including the sharp pointed end at the time of suturing a living tissue with a needle grasped by a needle holder.

BRIEF DESCRIPTION OF THE DRAWINGS

FIGS. 4(*c*) to 4(*d*) show partial cross-sectional views of the cutting-edge portion.

DESCRIPTION OF THE INVENTION

Figure 1A:
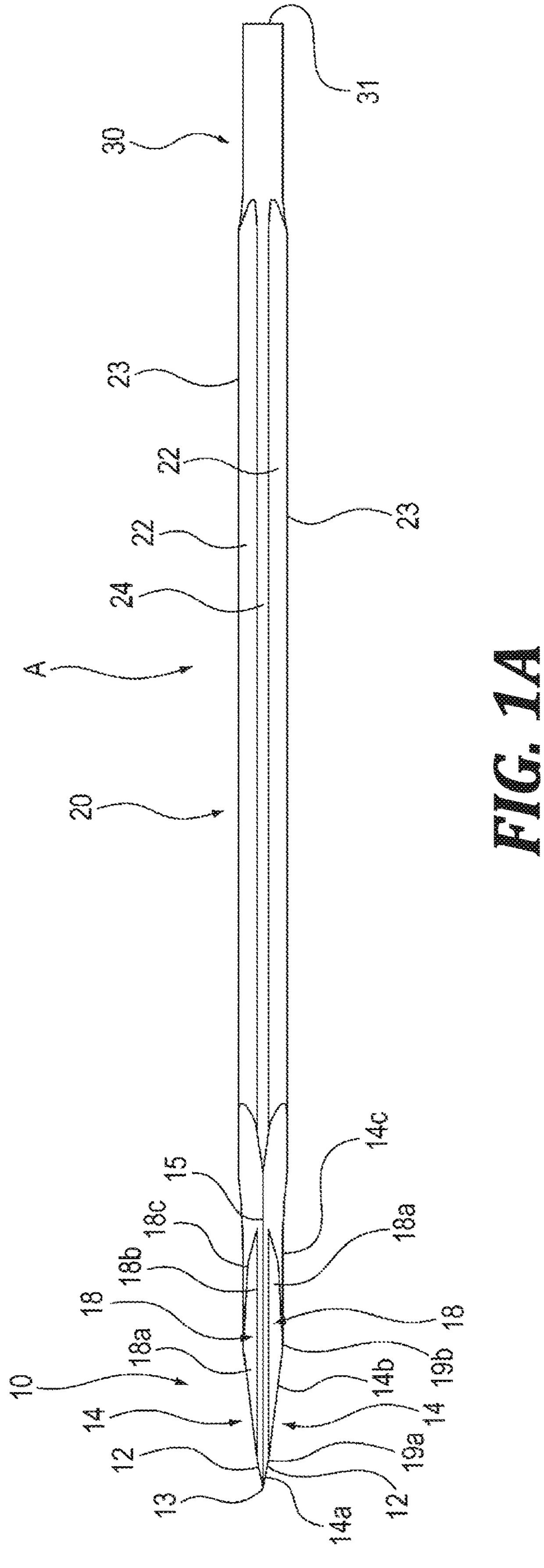
FIGS. 1(*a*) and 1 (*b*) show illustrative configurations of the suture needle according to the present example.
Figure 1B:
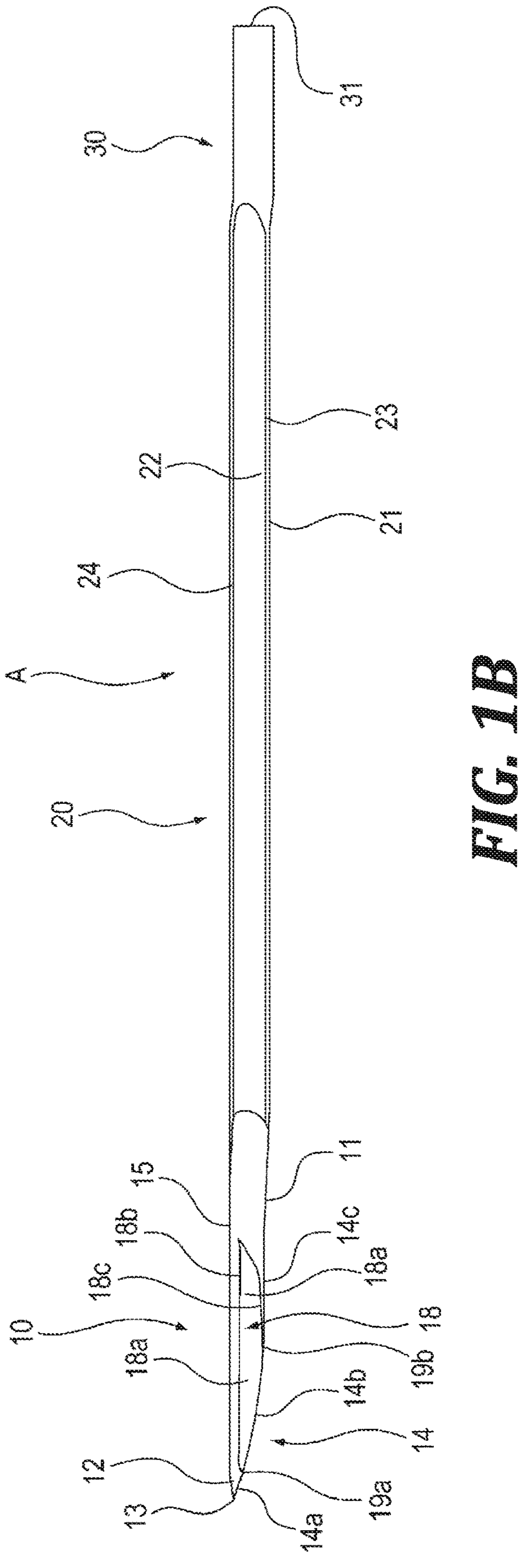
Figure 2:
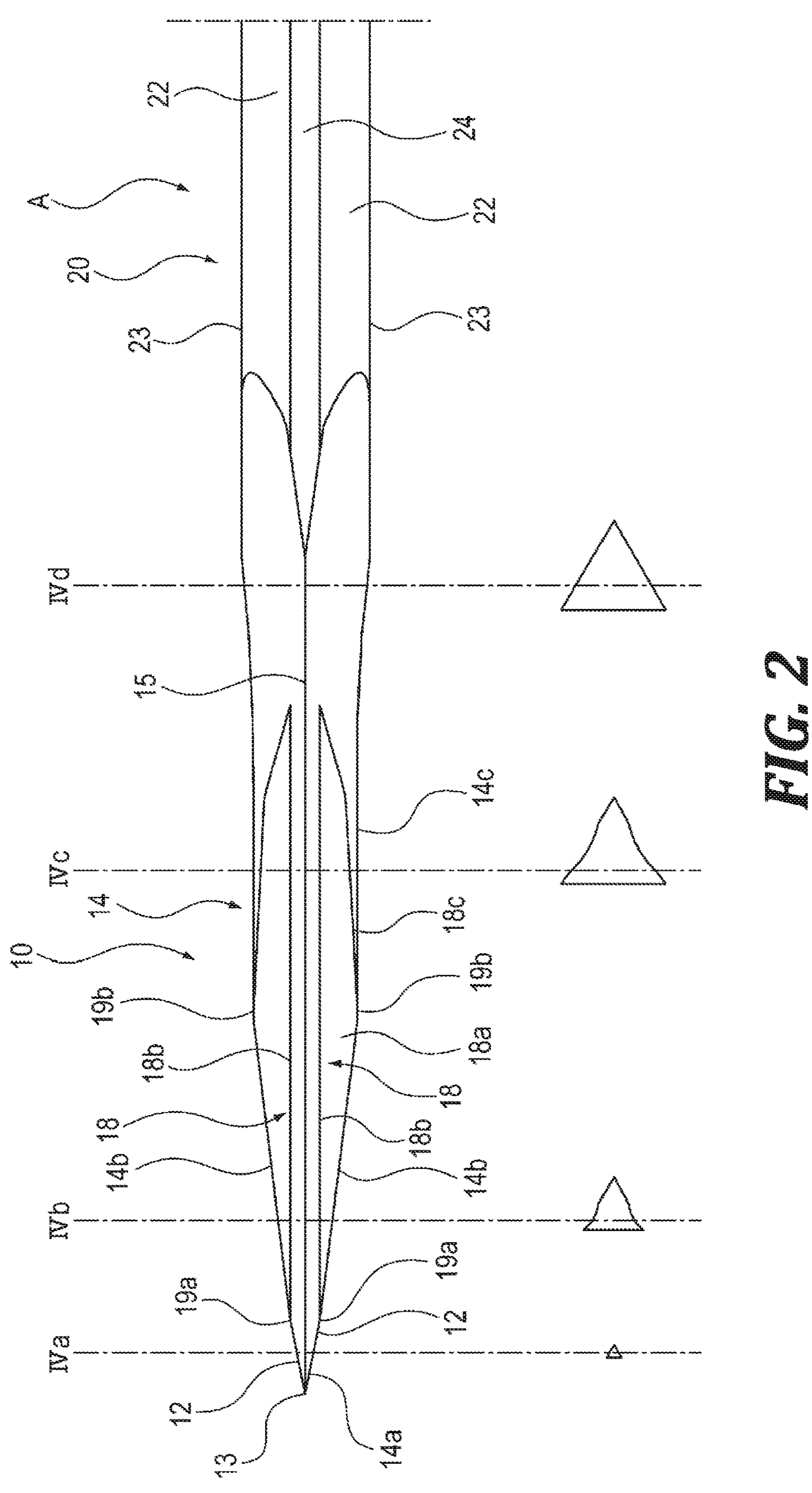
FIG. 2 shows an enlarged top view of the cutting-edge portion.
Figure 3:
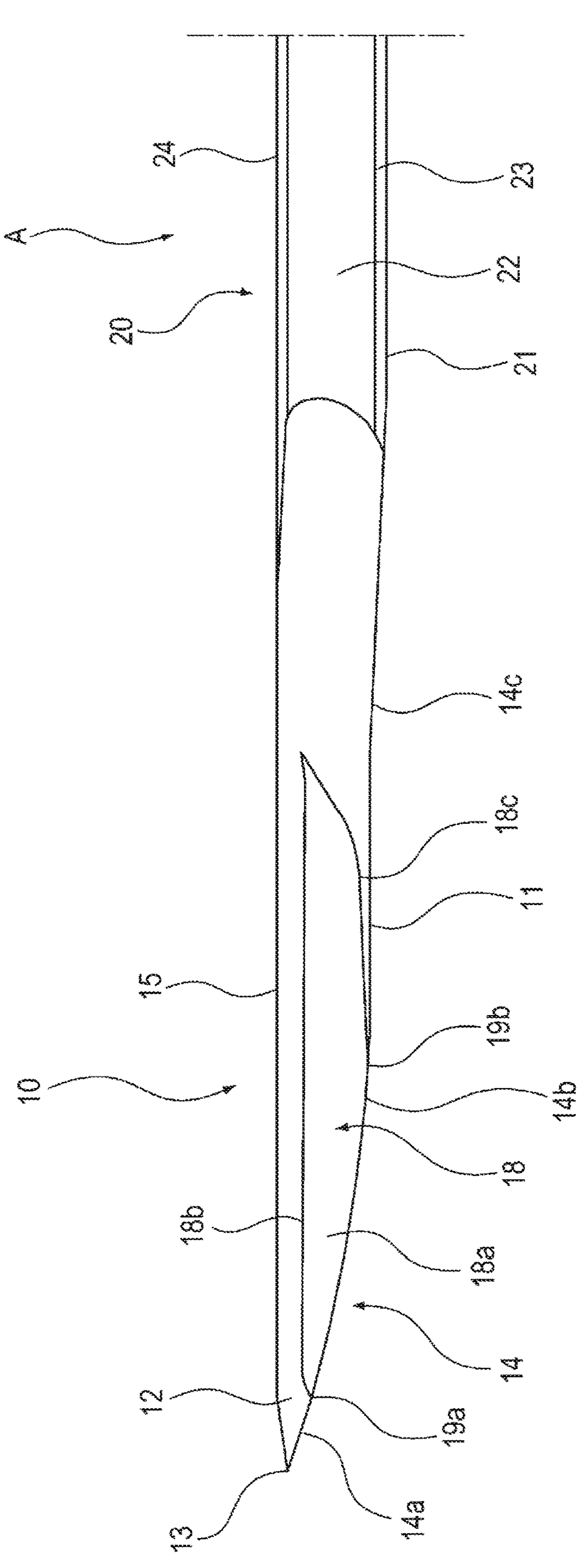
FIG. 3 shows an enlarged side view of the cutting-edge portion.

A suture needle according to the present invention will be described as follows. The suture needle of the present invention can reduce a risk of cracking or bending in a tip portion including a pointed end of a cutting-edge portion at a time of suturing a living tissue with a needle grasped by a needle holder.

In the present invention, it is not limited whether a desired suture needle is a curved needle with an arcuate curve or a straight needle with a straight line, and the suture needle may have any shape. If the desired suture needle is the curved needle, it is not also limited whether a top part is curved inside or outside.

The suture needle of the present invention includes a cutting-edge portion, a body portion continuously connected to the cutting-edge portion, and a base portion continuously connected to the body portion. The cutting-edge portion has a so-called tapered shape in which thickness thereof decreases from the body portion to the pointed end. The length and thickness of the cutting-edge portion are set appropriately to correspond to a desired size of the suture needle.

In the following explanation, "thickness" does not mean a diameter of a circle connecting vertices of across-sectional shape including a triangle, or a diameter of an inscribed circle of a cross-sectional shape, but a diameter of a circle having an area corresponding to an area of a cross-sectional shape.

The cutting-edge portion of the suture needle of the present invention has one bottom part, two slopes, and two curved grooves, in which each curved groove is configured on each of the two slopes. The tip portion configured by convergence of the one bottom part and two slopes is a sharp pointed end, and cutting-edges extend from the pointed end, in which each cutting-edge is configured by connection of the bottom part and each slope. In addition, the top part extends from the pointed end and is configured by connection of the two slopes, and thickness of the top part decreases from the body portion to the pointed end.

The groove on each of the two slopes has predetermined dimensions, and extends from a position on the cutting-edge isolated from the pointed end by a predetermined dimension toward the body portion, an upper portion of each groove is disposed along the top part, and a lower portion of each groove is isolated from each cutting-edge toward the top part as the lower portion extends toward the body portion. That is, the groove is located in the middle of the cutting-edge in the cutting-edge portion. Therefore, the cutting-edge located from the pointed end to a pointed-end-side end where the upper portion of the groove intersects the cutting-edge is configured by the bottom part and the slope, and the cutting-edge located from the body portion to a body-portion-side end where the lower portion of the groove intersects the cutting-edge is configured by the bottom part and the slope. In addition, the cutting-edge between the pointed-end-side end and the body-portion-side end of the groove is configured by the bottom part and a curved surface constituting the groove.

In the present invention, a dimension of the groove configured in the slope needs to be smaller than the maximum dimension of the slope, but not limited to any particular dimensions. The position of the groove in the cutting-edge is not particularly limited, but a distance from a tip of the body-portion-side end where the lower portion of the groove intersects the cutting-edge, is preferably about 2.5 to 5 times longer than thickness D of the suture needle. A distance from a tip of pointed-end-side end where the upper portion of the groove intersects the cutting-edge, is set according to the aforementioned dimension from the tip on the body-portion-side end in the cutting-edge and a width dimension of the groove.

A method for forming the curved grooves on the two slopes is not particularly limited, and a grinding method and a pressing method can be selectively employed. However, in consideration of the ease of processing and the improvement of strength accompanying the processing, it is preferable to use a press process. In this case, if the groove is made too deep, the processing rate becomes excessive and is not desirable.

After the bottom part and the two slopes constituting the cutting-edges are formed by the press process, one of the surfaces may be formed as a grinding surface and another surface may be left as a pressing surface, or all the surfaces may be formed as the grinding surface. After the press process, the two slopes can be ground, the curved grooves can be formed by press process, and then the bottom part can be ground. In that case, the groove is ground by increasing the amount of grinding on the pointed end side so that the groove becomes shallower toward the pointed end side. By forming the grooves in this manner, bulges around the grooves, which are generated after the grooves are pressed, can be removed.

As described above, by using the two slopes constituting the cutting-edge portion as grinding surfaces, and matching these grinding surfaces with each other, the top part sandwiched by the slopes may be formed as a cutting-edge. Also, the top part without a function as a cutting-edge can be formed by keeping the two grinding surfaces apart without matching them.

In the present invention, there is no particular limitation as to material of the suture needle, and any material having moderate strength such as stainless steel and spring steel can be selectively utilized. However, from the viewpoint of rusting, it is preferable to use stainless steel, and in particular, it is preferable to use a wire rod having thickness of a desired suture needle and having a structure elongated into a fiber shape by cold wire drawing of a round bar made of austenitic stainless steel at a predetermined surface reduction ratio.

The configuration of the suture needle in the present example is described below based on the figures. Suture needles A shown in the figures have a straight shape. The suture needles A is used as a suture needle in this state, or the straight suture needle A is bent in a subsequent process to be used as a curved suture needle.

The suture needle A in the present example is formed by cutting a wire rod made of austenitic stainless steel, which has been cold-wired to a preset diameter, to a predetermined length; pressing one end side thereof to form a material having a triangular prism shape; grinding the material; and applying a stop-hole process to the material.

The suture needle A has a cutting-edge portion 10 configured on one side thereof, a body portion 20 configured to be continuously connected to the cutting-edge portion 10, and a base portion 30 configured to be continuously connected to the body portion 20, in which a suture thread not shown in the figures is attached to the base portion 30. The cutting-edge portion 10 has a function of piercing and incising a biological tissue when suturing the biological tissue. The body portion 20 has a function of connecting the cutting-edge portion 10 to the base portion 30, and is configured to have substantially the same cross-sectional shape as that of the cutting-edge portion 10.

The base portion 30 has a circular cross-section, and a stop hole (not shown) on the end face 31. The suture thread is attached by inserting the end of the suture thread into the stop hole and crimping a section corresponding to the stop hole in the base portion 30. However, the structure for attaching the suture thread to the suture needle is not limited to the present example, and it is natural that the structure for attaching the suture thread to the suture needle may also be a structure in which the base portion 30 has a flat section and a pair of pillars with spring characteristic on the flat section, and the suture thread can be passed between the pillars.

The cutting-edge portion 10 has one bottom part 11, two slopes 12, a sharp pointed end 13 configured by convergence of the one bottom part and two slopes at a tip thereof, and cutting-edges 14 extending from the pointed end 13, in which each cutting-edge is configured by connection of the bottom part and each slope. That is, each cutting-edge 14 is located, from the pointed end 13 to the body portion 20, on each side of the bottom part 11 in a width direction thereof.

The cutting-edge portion 10 has a tapered shape such that thickness of the cutting-edge portion decreases from the body portion 20 to the pointed end 13. That is, the cutting-edge portion 10 has a shape of a triangular pyramid having the pointed end 13 as an apex, and when the suture needle is viewed from the pointed end 13 side, the cutting-edge portion 10 is within the cross-section of the body portion 20 so that there are no parts protruding from both sides of the body portion 20. This can reduce a puncture mark.

The two slopes 12 constituting the cutting-edge portion 10 are connected each other to configure a top part 15. The top part 15 may be configured to be capable of functioning as a cutting-edge, or it may be configured not to function as a cutting-edge.

As shown in the figures, the bottom part 11 extends, in the cutting-edge portion 10, from the body portion 20 side toward the pointed end 13 so as to approach the top part 15, and the top part 15 extends slightly downward toward the bottom part 11 side in the vicinity of the pointed end 13. As a result, the cutting-edge portion 10 has the shape of the triangular pyramid having the pointed end 13 as the apex.

An angle between the two slopes 12 constituting the top part 15 is not limited to any particular angle. However, the angle is preferably the same as that of each cutting-edge 14 configured on both sides of the bottom part 11 located in the width direction of the bottom part 11 in order to ensure balanced and even insertion property. For this reason, the angle between the two slopes 12 is preferably in the range of 60 degrees plus or minus a moderate angle.

Each of the two slope 12 has the groove 18 with a curved surface **18*a* along the top part 15. As described above, the grooves 18 have dimensions smaller than the width dimension of each slope 12, which are configured along the top part 15. Since the bottom part 11 approaches the top part 15 side as it approaches the pointed end 13, an upper portion 18*b* of each groove 18 intersects the cutting-edge 14 to configure the pointed-end-side end 19*a* at an intersection site, and a lower edge 18*c* intersects the cutting-edge 14 to configure the body-portion-side end 19*b* at an intersection site. Further, as the groove 18 approaches the body portion 20, the lower edge 18*c* detaches from the cutting-edge 14 at the body-portion-side end 19*b* and separates from the top part 15** side.

Each groove 18 includes the curved surface **18*a* concavely configured on each slope 12. A method for forming the concave groove 18 with the curved surface 18*a* on each slope 12 is not particularly limited to any particular method, and can be formed by grinding or pressing each slope 12. In the present example, each groove 18 is formed on each slope 12 by press process. After the grooves 18 are formed, the bottom part 11 is formed to give the cutting-edge 14** a function as a cutting-edge.

A portion where each groove 18 intersects the cutting-edge 14, which is sandwiched between the body-portion-side end **19*b* and the pointed-end-side end 19*a* in the cutting-edge 14, has a loose curve in top view, and a cutting-edge 14*b* is configured in this portion where the bottom part 11 is connected with the curved surface 18*a***.

Accordingly, the cutting-edge 14 is continuously composed of a cutting-edge **14*a* where the bottom surface 11 is connected with the slope 12, the cutting-edge 14*a* extending between the pointed end 13 and the pointed-end-side end 19*a*, the cutting-edges 14*b* extending between the pointed-end-side end 19*a* and the body-portion-side end 19*b*, and cutting-edges 14***c* where the bottom part 11 is connected with each slope 12, each cutting-edge 14*c* extending from the body-portion-side end 19*b* to the body portion 20.

Figure 4B:
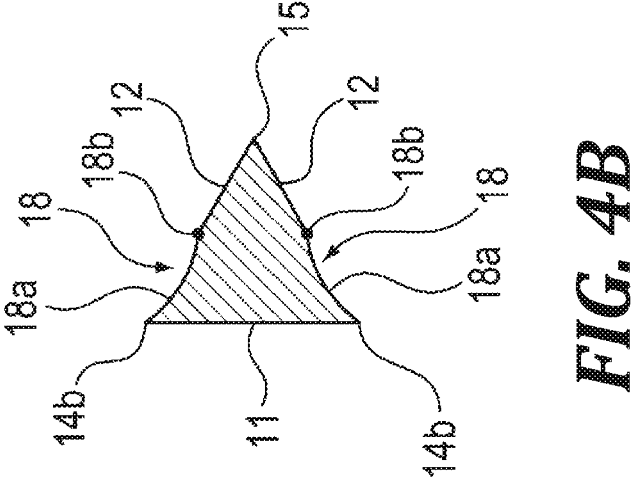
FIGS. 4(*a*) to 4(*b*) show partial cross-sectional views of the cutting-edge portion.
Figure 4A:
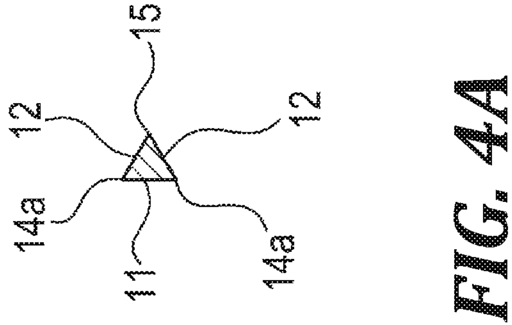
Figure 4D:
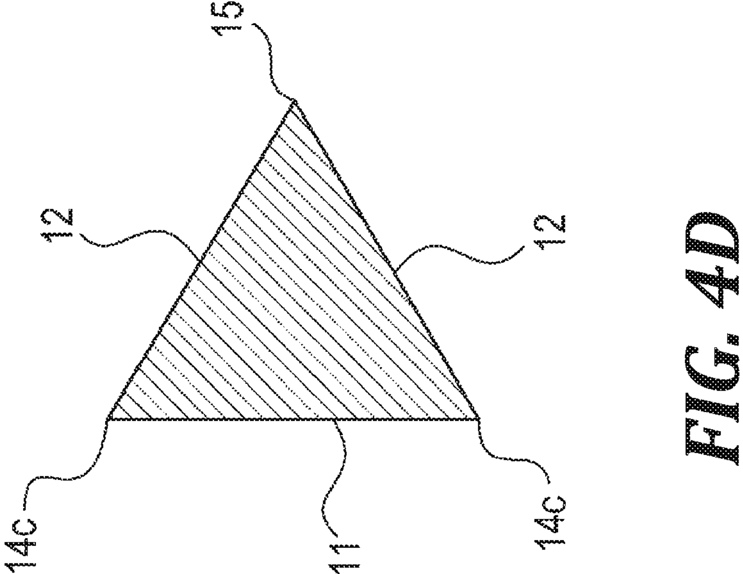
Figure 4C:
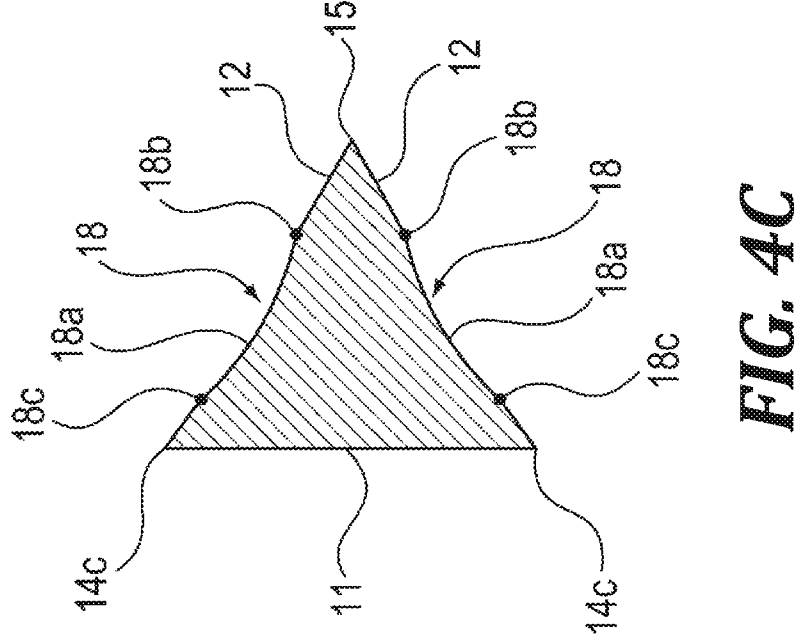

For this reason, a shape of the cross-section of the cutting-edge portion 10 between the pointed end 13 and the pointed-end-side end 19*a* is a triangle (a generally equilateral triangle in this example) having the two cutting-edges 14*a* and the top part 15 as vertices, as shown in FIG. 4(*a*). Also, a shape of the cross-section of the cutting-edge portion 10 on the body portion 20 side from the groove 18 is a generally equilateral triangle having the two cutting-edges 14*c* and the top part 15 as vertices, as shown in FIG. 4(*d*).

As shown in FIG. 4(*b*), the cross-section of the cutting-edge portion 10 between the pointed-end-side end 19*a* and the body-portion-side end 19*b* has a generally pentagonal shape in which the slopes 18*a* of grooves 18 extend below the slopes 12 constituting the top part 15. The bottom part 11 is connected with each curved surface 18*a* constituting the groove 18 to configure each cutting-edge 14*b*. In particular, since the bottom part 11 is connected with each curved surface 18*a* to configure each cutting-edge 14*b*, the cutting-edge can have a sharper edge than an edge configured by connection of the planes, described in Patent Document 3.

In a portion having each groove 18 from the body-portion-side end 19*b* toward the body portion 20 side (a portion adjacent to the body portion 20 side of the body-portion-side end 19*b*), the cross-section of the cutting-edge portion 10 has a generally equilateral triangle having the grooves 18 on the slope 12 surfaces, as shown in FIG. 4(*c*). Each cutting-edges 14*c* has the same angle as each cutting-edge 14*a* extending between the pointed end 13 and the pointed-end-side end 19*a* and extends from each cutting-edge 14*a*.

In particular, the angle of each cutting-edge 14*c* at the portion adjacent to the body portion 20 side of the body-portion-side end 19*b* is larger than that of each cutting-edge 14*b* at the portion adjacent to the sharp end 13 side of the body-portion-side end 19*b*. In other words, the angle of each cutting-edge 14*b* between the pointed-end-side end 19*a* and the body-portion-side end 19*b* is smaller than that of each cutting-edge 14*c*.

The suture needle A configured as described above is difficult to bend in the portion adjacent to the body portion 20 side of the body-portion-side end 19*b*, which may bend when grasped by the needle holder. As a result, the reliability of the suture needle A is improved compared with that of the suture needle described in Patent Document 3.

The inventor of the present invention conducted a comparison test between the suture needle A of the present invention and the suture needle described in Patent Document 3 as a conventional suture needle. Both suture needles had the same standard size, and the relationship between the bending moment and the bending angle was measured by grasping a position 3 mm away from the pointed end with the needle holder and applying a force to the tip.

In the suture needle of the present invention, the bending moment when bent by 20 degrees was abbreviated to 35 mNm, and the bending moment when bent by 90 degrees was abbreviated to 40 mNm. In the compared suture needle, the bending moment when bent by 20 degrees was abbreviated to 25 mNm, and it yielded when bent by 50 degrees. From these comparative results, it can be said that the suture needle of the present invention can exhibit sufficient bending strength.

The body portion 20 has a press-processed bottom part 21 and two slopes 22, and the bottom part 21 is connected with the slopes 22 via curved surfaces 23 (R surface), and the two slopes 22 are also connected each other via a top part 24 having curved surfaces. Therefore, each curved surface 23 and 24 do not have a function as a cutting-edge.

INDUSTRIAL APPLICABILITY

The suture needle A of the present invention can be used as a straight suture needle or as a curved suture needle.

DESCRIPTION OF THE REFERENCE NUMERAL

A Suture Needle
10 Cutting-edge portion
11, 21 Bottom part
12, 22 Slope
13 Pointed end
14, 14*a* to 14*c* Cutting-edge
15 Top part
18 Groove
18*a* Curved surface
18*b* Upper portion
18*c* Lower portion
19*a* Pointed-end-side end
19*b* Body-portion-side end
20 Body portion
23, 24 Curved surface
30 Base portion
31 End face

The invention claimed is:

1. A medical suture needle comprising a cutting-edge portion and a body portion continuously connected to the cutting-edge portion, wherein the cutting-edge portion comprises:

one bottom part;

two slopes;

a sharp pointed end configured by convergence of the bottom part and the two slopes;

cutting-edges extending from the sharp pointed end, each cutting-edge being configured by connection of the bottom part and each slope;

a top part extending from the sharp pointed end and configured by connection of the two slopes, thickness of the cutting-edge portion decreases from the body portion to the sharp pointed end, each slope comprises a curved groove having a predetermined dimension, each curved groove extends, along the top part, from a position on the cutting-edge isolated from the sharp pointed end by a predetermined distance, each cutting-edge between a pointed-end-side end and a body-portion-side end of the curved groove is configured by the bottom part and a curved surface constituting the curved groove, a lower portion of each curved groove is defined by a bottom edge of a contour of the groove and is isolated from the cutting edge toward the top part as the lower portion extends from a position on a body-portion-side end of each curved groove toward the body portion, whereby each cutting-edge located from the body-portion-side end to the body portion is configured by the bottom part and each slope, and a cross-section of the cutting-edge portion has: a triangle shape between the pointed end and the pointed-end-side end; a pentagonal shape between the pointed-end-side end and the body-portion-side end; and a triangle shape in each cutting-edge located from the body-portion-side end to the body portion.

2. The medical suture needle according to claim 1, wherein each of the two slopes of the cutting-edge portion has a grinding surface, and each groove on the two slopes has a pressing surface.

3. The medical suture needle according to claim 1, wherein each cutting-edge at the body-portion-side end is configured by the bottom part and a lower portion of a curved surface constituting each groove, and an angle of each cutting-edge at the portion adjacent to the body portion side of the body-portion-side end is larger than that of each cutting-edge at the portion adjacent to the sharp end side of the body-portion-side end.

* * * * *